(12) United States Patent
Khettal et al.

(10) Patent No.: US 10,993,604 B2
(45) Date of Patent: May 4, 2021

(54) CAMERA OBJECTIVE LENS FOR AN ENDOSCOPE

(71) Applicant: avateramedical GmbH, Jena (DE)

(72) Inventors: Ali Khettal, Berlin (DE); Fabian Weise, Berlin (DE)

(73) Assignee: avateramedical GmbH, Berlin (DE)

( * ) Notice: Subject to any disclaimer, the term of this patent is extended or adjusted under 35 U.S.C. 154(b) by 388 days.

(21) Appl. No.: 16/008,802

(22) Filed: Jun. 14, 2018

(65) Prior Publication Data

US 2018/0360297 A1    Dec. 20, 2018

(30) Foreign Application Priority Data

Jun. 16, 2017   (DE) .......................... 102017113274.0

(51) Int. Cl.
*G02B 9/64* (2006.01)
*H04N 5/225* (2006.01)
(Continued)

(52) U.S. Cl.
CPC .......... *A61B 1/00096* (2013.01); *A61B 1/002* (2013.01); *A61B 1/00163* (2013.01); *A61B 1/00193* (2013.01); *A61B 1/042* (2013.01); *G02B 9/64* (2013.01); *G02B 13/0095* (2013.01); *G02B 23/243* (2013.01); *G02B 23/2415* (2013.01); *G02B 23/2453* (2013.01); *G02B 27/0955* (2013.01); *G02B 27/0972* (2013.01);
(Continued)

(58) Field of Classification Search
CPC combination set(s) only.
See application file for complete search history.

(56) References Cited

U.S. PATENT DOCUMENTS 4,898,457 A * 2/1990 Alexeev ................. G02B 13/16
                                                                    313/371
7,085,072 B2 * 8/2006 Kuba .................... G02B 13/002
                                                                    359/686
(Continued)

FOREIGN PATENT DOCUMENTS

DE        3529026 C2    5/1897
DE    102015118199 A1    4/2017
(Continued)

*Primary Examiner* — Anh Tuan T Nguyen
*Assistant Examiner* — Shankar Raj Ghimire
(74) *Attorney, Agent, or Firm* — McGarry Bair PC

(57) ABSTRACT

A camera objective lens for an endoscope has an object-side first prism and an image-side second prism, a first lens system arranged on the object side of the first prism and a second lens system arranged on the image side of the first prism, and a sensor surface arranged at the image-side end of the camera objective lens parallel to the longitudinal axis of an endoscope shaft of the endoscope. The first prism and the second prism are designed to cause a first to third beam deflection as a three-fold beam deflection. The first lens system includes a biconcave first lens, a biconvex second lens, a third lens formed as a rod lens, a plane-concave fourth lens and a biconvex fifth lens in this order as viewed from the object side. The second lens system includes a convex-plane sixth lens, a seventh lens formed as a meniscus lens, a biconvex eighth lens and a biconcave ninth lens in this order as viewed from the object side.

15 Claims, 3 Drawing Sheets

(51) Int. Cl.
  *A61B 1/00*   (2006.01)
  *G02B 13/00*  (2006.01)
  *G02B 27/09*  (2006.01)
  *G02B 23/24*  (2006.01)
  *A61B 1/04*   (2006.01)
  *A61B 1/002*  (2006.01)

(52) U.S. Cl.
  CPC ........ H04N 5/2254 (2013.01); *A61B 1/00188* (2013.01)

(56) References Cited

U.S. PATENT DOCUMENTS

| | | | | |
|---|---|---|---|---|
| 8,345,357 | B2* | 1/2013 | Imaoka | G02B 15/163 |
| | | | | 359/754 |
| 2003/0189766 | A1* | 10/2003 | Nishioka | G02B 13/009 |
| | | | | 359/726 |
| 2003/0197802 | A1* | 10/2003 | Kato | G02B 13/005 |
| | | | | 348/335 |
| 2004/0095503 | A1* | 5/2004 | Iwasawa | G02B 13/004 |
| | | | | 348/344 |
| 2004/0257677 | A1* | 12/2004 | Matsusaka | H04N 5/23299 |
| | | | | 359/783 |
| 2005/0030405 | A1* | 2/2005 | Morooka | H04N 5/2254 |
| | | | | 348/335 |
| 2006/0017834 | A1* | 1/2006 | Konno | G02B 13/003 |
| | | | | 348/335 |
| 2007/0064315 | A1* | 3/2007 | Kobayashi | G02B 13/004 |
| | | | | 359/689 |
| 2009/0102961 | A1* | 4/2009 | Uzawa | G02B 23/243 |
| | | | | 348/345 |
| 2010/0053774 | A1* | 3/2010 | Baba | G02B 13/16 |
| | | | | 359/755 |
| 2014/0253761 | A1* | 9/2014 | Okada | H04N 5/23287 |
| | | | | 348/240.2 |
| 2015/0198784 | A1* | 7/2015 | Bone | G02B 13/006 |
| | | | | 359/708 |
| 2016/0004054 | A1 | 1/2016 | Kawamura | |
| 2017/0049306 | A1* | 2/2017 | Katakura | A61B 1/00193 |
| 2017/0329124 | A1* | 11/2017 | Morita | A61B 1/00096 |
| 2017/0351086 | A1* | 12/2017 | Takahashi | A61B 1/00101 |
| 2017/0359566 | A1* | 12/2017 | Goma | H04N 13/271 |
| 2018/0017777 | A1* | 1/2018 | Takasugi | A61B 1/00188 |
| 2018/0031813 | A1* | 2/2018 | Morooka | G02B 21/361 |
| 2019/0033563 | A1* | 1/2019 | Ichikawa | G02B 9/62 |
| 2019/0196148 | A1* | 6/2019 | Yao | H04N 5/2254 |
| 2020/0008660 | A1* | 1/2020 | Uchida | G02B 23/2415 |
| 2020/0018947 | A1* | 1/2020 | Tsuyuki | H04N 5/2254 |
| 2020/0138275 | A1* | 5/2020 | Homma | H04N 7/18 |

FOREIGN PATENT DOCUMENTS

| | | |
|---|---|---|
| EP | 0667547 A2 | 1/1995 |
| EP | 2293130 A1 | 3/2011 |
| EP | 3162273 A1 | 5/2017 |
| JP | 6160731 | 6/1994 |

* cited by examiner

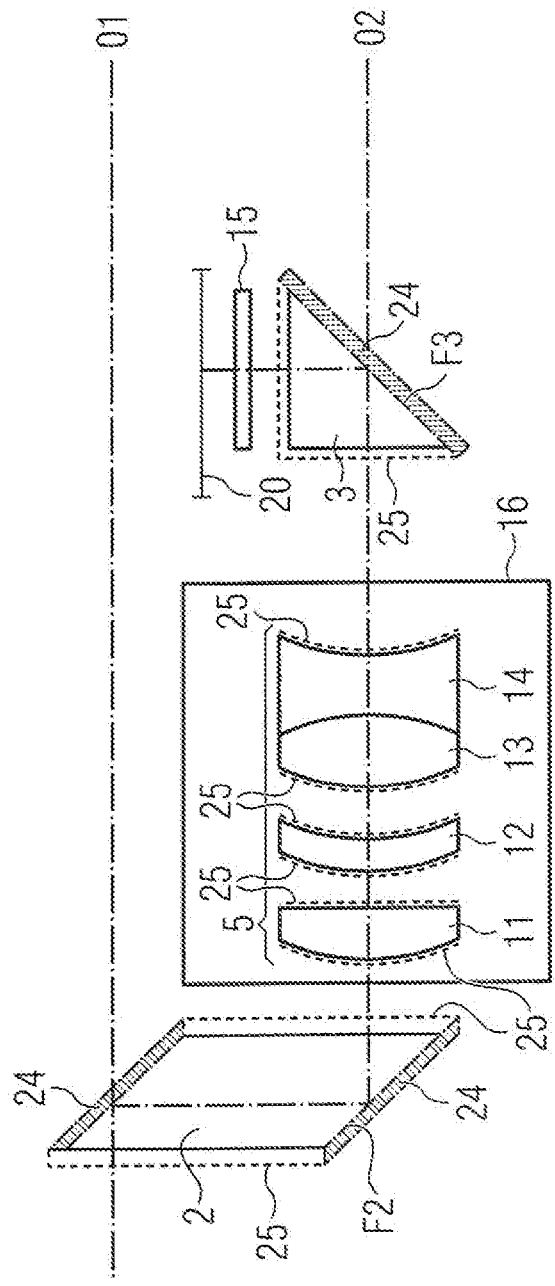
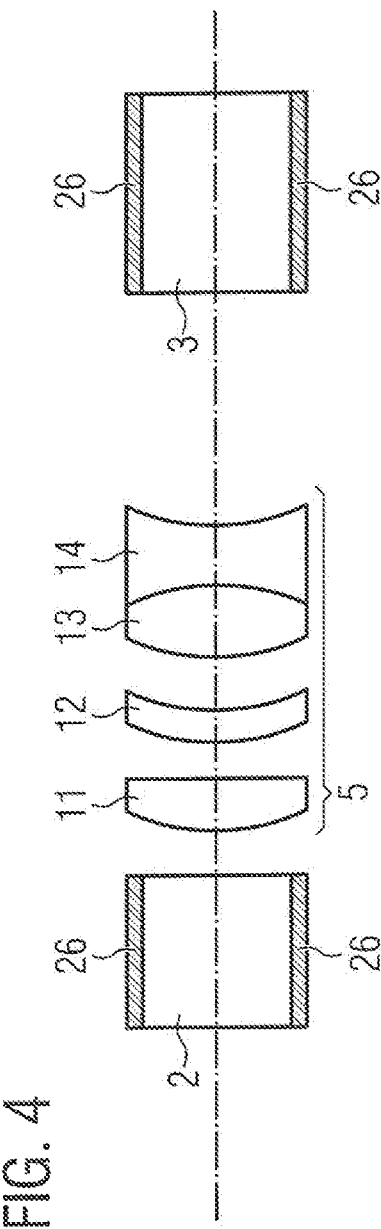

CAMERA OBJECTIVE LENS FOR AN ENDOSCOPE

CROSS REFERENCE TO RELATED APPLICATIONS

This application claims the benefit of German Application DE 10 2017 113 274.0, filed on Jun. 16, 2017, which is incorporated herein in its entirety.

BACKGROUND

The invention relates to a camera objective lens for an endoscope having an object-side first prism, an image-side second prism, a first lens system arranged on the object side of the first prism, a second lens system arranged on the image side of the first prism, and a sensor surface arranged at the image-side end of the camera objective lens parallel to the longitudinal axis of an endoscope shaft of the endoscope.

Endoscopes are in particular used in minimally invasive surgery to allow the operating surgeon insight into the body region in which the operating field is situated. Both monocular endoscopes and stereoscopic endoscopes are used, the latter providing a three-dimensional impression of the depth via two optical channels, which is not possible with monocular endoscopes.

At the distal end of an endoscope shaft, typically an objective lens is arranged, which collects the light originating from the object to be observed and generates a real intermediate image of the object. This intermediate image is transmitted by means of an optical relay system arranged downstream of the objective lens to the proximal end of the endoscope shaft. An eyepiece, which images the real intermediate image for the human eye, is arranged at the proximal end of the endoscope shaft. Instead of a mere optical eyepiece, the eyepiece may also include a camera adapter with a suitable image sensor which makes it possible to view the image on a screen and to store video information.

Typically, both monocular endoscopes and stereoscopic endoscopes that provide additional depth information are used to enable an accurate operation.

From document JP 6-160731, a stereoscopic endoscope is known, which has two identical relay optical systems which optically guide an image from an objective lens to an eyepiece. The eyepiece includes a prism system which images by means of two beam deflections and in a parallel offset manner the real intermediate images generated by the relay optical system onto two sensor surfaces arranged orthogonally to the optical axis O of the endoscope.

A similar arrangement with two adjustable prisms for beam deflection onto sensor surfaces arranged orthogonally to the optical axis is disclosed in document EP 0 667 547 A2.

In the prior art, further an eyepiece in combination with an adapter for an endoscope is disclosed, which by a one-time beam deflection with the aid of a mirror inclined by 45° images the intermediate image of the relay optical system onto a sensor surface arranged parallel to the optical axis.

In document DE 35 29 026 C2, a camera objective lens for an endoscope is disclosed, which images by a four-fold beam deflection by means of a prism system the intermediate image of the relay optical system onto a sensor surface arranged parallel to the optical axis. In document DE 35 29 026 C2, further a camera objective lens with a three-fold beam deflection is disclosed, in which optical component parts are arranged parallel to the optical axis between the second and the third beam deflection.

In endoscopy, the shaft, at the proximal end of which the objective lens is provided and which comprises the relay optical system, should have a diameter as small as possible. In contrast thereto, the sensor surface should have a certain size for technical reasons. The intermediate image of the relay optical system has to be magnified prior to the imaging onto the sensor surface. This magnification is typically accompanied by a loss of optical quality.

SUMMARY OF THE INVENTION

It is the object of the invention to specify a camera objective lens for an endoscope, which has a compact structure and by means of which a loss in optical quality during magnification can be avoided.

This object is solved by a camera objective lens having the features of claim 1 and a monocular endoscope or stereoscopic endoscope having the features of claim 15. Advantageous developments are specified in the dependent claims.

The camera objective lens according to the invention comprises:
   a first optical axis which is defined by the longitudinal axis of an endoscope shaft, and a second optical axis which is offset relative to the first optical axis,
   an object-side first prism and an image-side second prism,
   a first lens system arranged on the object side of the first prism and a second lens system arranged on the image side of the first prism, wherein the first lens system is arranged along the first optical axis, and wherein the second lens system is arranged along the second optical axis, and
   a sensor surface arranged at the image-side end of the camera objective lens parallel to the first optical axis,
   characterized in that the first prism and the second prism are configured to cause a first to third beam deflection as a three-fold beam deflection so that by means of the first prism the first and second beam deflection is caused as a two-fold beam deflection from the first optical axis to the second optical axis and by means of the second prism the third beam deflection is caused as a simple beam deflection from the second optical axis to the sensor surface arranged parallel to the first optical axis,
   that the first lens system includes a biconcave first lens, a biconvex second lens, a third lens formed as a rod lens, a plane-concave fourth lens and a biconvex fifth lens in this order as viewed from the object side,
   and that the second lens system includes a convex-plane sixth lens, a seventh lens formed as a meniscus lens, a biconvex eighth lens and a biconcave ninth lens in this order as viewed from the object side.

The three-fold beam deflection allows a particularly compact arrangement of the optical elements within the camera objective lens. In particular in a camera objective lens for a stereoscopic endoscope a particularly compact structure is obtained by the eccentric arrangement of the second lens system (adapter optical system). The arrangement of the sensor surface parallel to the optical axis of the endoscope allows a compact structure of the distal end both in monocular and in stereoscopic endoscopes. The first lens system (eyepiece optical system) is additionally formed such that it corrects possibly existing image errors of the objective lens and/or of the relay optical system. In particular, a still present positive image field curvature is compensated by the negative image field curvature of the eyepiece optical system. As a result, a compact structure of the camera objective lens is obtained. At the same time, by means of it, a loss in optical quality during magnification can be avoided. In particular, the first lens system is an eyepiece optical system and the second lens system is an adapter optical system. The eyepiece optical system forms together with the adapter optical system the camera objective lens.

The arrangement of a rod lens as a part of the eyepiece optical system moreover enables an adaptation of the length of the endoscope without the shaft diameter having to be increased.

In a possible advantageous embodiment, the biconcave first lens and the biconvex second lens of the eyepiece optical system are cemented to each other and chromatically corrected. Further, the third lens, the plane-concave fourth lens and the biconvex fifth lens of the eyepiece optical system can be cemented to each other and chromatically corrected.

Further, it is advantageous when the biconvex eighth lens and the biconcave ninth lens of the adapter optical system are likewise cemented to each other and are chromatically corrected.

In an advantageous development, the rod lens and the plane-concave fourth lens of the eyepiece optical system are cemented to each other. This cementation of optical elements into one cemented component makes an easy assembly of the same in the endoscope possible. In particular, the design of the rod lens and of the cemented component with one planar surface each makes it possible to set the pointing in one adjustment step by a lateral displacement. For this, the cemented component bears thereon and needs no further mount since it can directly be cemented after adjustment. This is in particular important for stereoendoscopes. By the axial displacement of the eyepiece optical system 4, the sharpness can be set to a distance in particular during assembly.

It is advantageous to arrange a plane-parallel glass plate parallel to the sensor surface for protection thereof.

For example, one or more lenses of the eyepiece optical system and/or one or more lenses of the adapter optical system have an antireflection coating on their outer surfaces that are exposed to air. As a result, scattered light and the associated reduction of the optical quality of the endoscope are minimized. Further, the antireflection coating increases the optical transmission.

For example, one or more surfaces of the first and second prism, respectively, comprise a high-reflection coating. This serves to reflect as much light as possible during the beam deflections and to increase the optical quality of the system.

It is advantageous when one or more surfaces of the first prism and/or of the second prism that are parallel to the first optical axis and perpendicular to the sensor surface have a matt black coating. This, too, serves to minimize scattered light and the associated reduction of the optical quality of the endoscope.

Further, it is advantageous when one or more optical components of the camera optical system are made of flint glass or crown glass. On the one hand, the high dispersion of flint glasses allows the construction of the respective lens system with desired achromatic properties, in particular by the combination of lighter and heavier flint glasses with different Abbe number and refractive index. On the other hand, the use of in particular barium crown glass is advantageous due to its optical transmission properties.

In a further advantageous development, a device for adjusting image sharpness and magnification is arranged in the adapter optical system. In particular in a stereoscopic endoscope, thus the image sharpness and magnification can be adjusted separately for each of the two image channels. The image sharpness can also be set by displacing the image sensor.

The invention further relates to a stereoscopic camera objective lens including two camera objective lenses of the above-described type arranged in pairs.

A further aspect of the invention relates to a monocular endoscope or stereoscopic endoscope. The monocular endoscope comprises a camera objective lens as previously described. The stereoscopic endoscope comprises the just mentioned stereoscopic camera objective lens.

Further features and advantages of the invention result from the following description which explains the invention in more detail on the basis of embodiments in connection with the enclosed Figures.

DRAWINGS

FIG. 3 shows the camera objective lens according to FIG. 1 with a view plane orthogonal to the sensor surface without illustration of the eyepiece optical system;

FIG. 4 shows the camera objective lens according to FIG. 1 with a view plane parallel to the sensor surface without illustration of the eyepiece optical system;

DESCRIPTION

Figure 1:
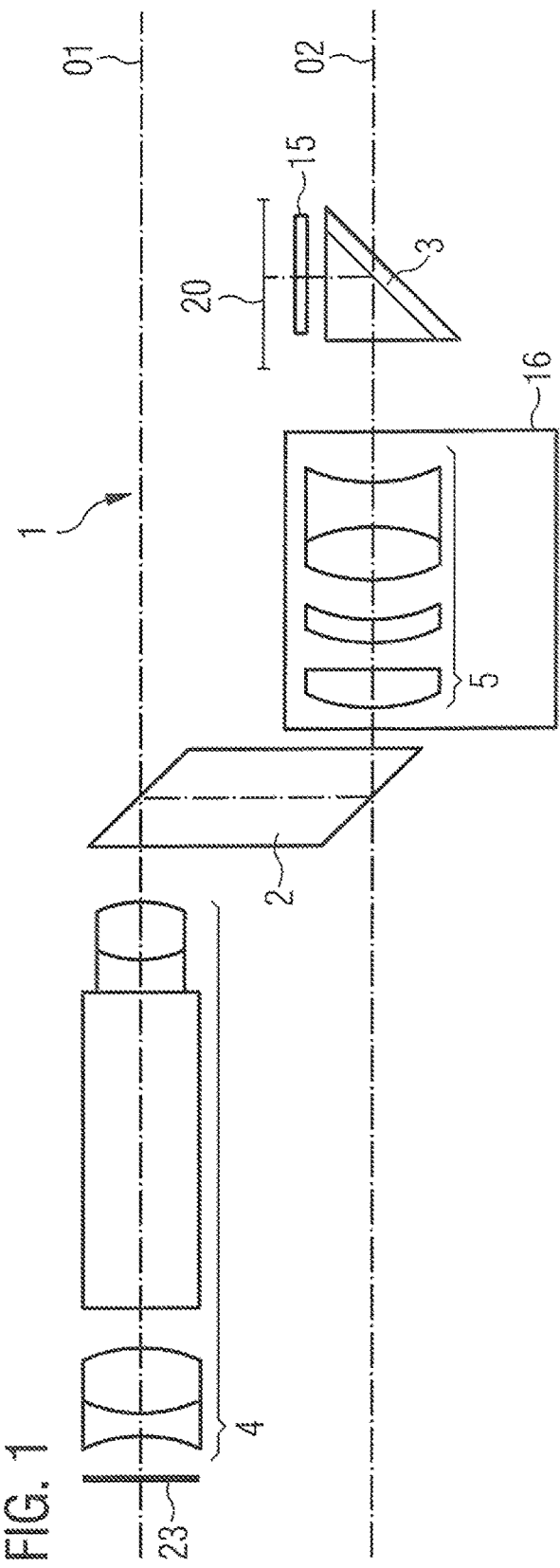
FIG. 1 shows a camera objective lens according to one embodiment.

A camera objective lens 1 is schematically illustrated in FIG. 1 in one possible embodiment. The camera objective lens 1 comprises an eyepiece optical system 4, an object-side prism 2, an adapter optical system 5, an image-side prism 3 and a sensor surface 20. Also shown is the intermediate image 23 of an optical relay system arranged upstream of the camera objective lens 1 and not illustrated in FIG. 1.

Figure 2:
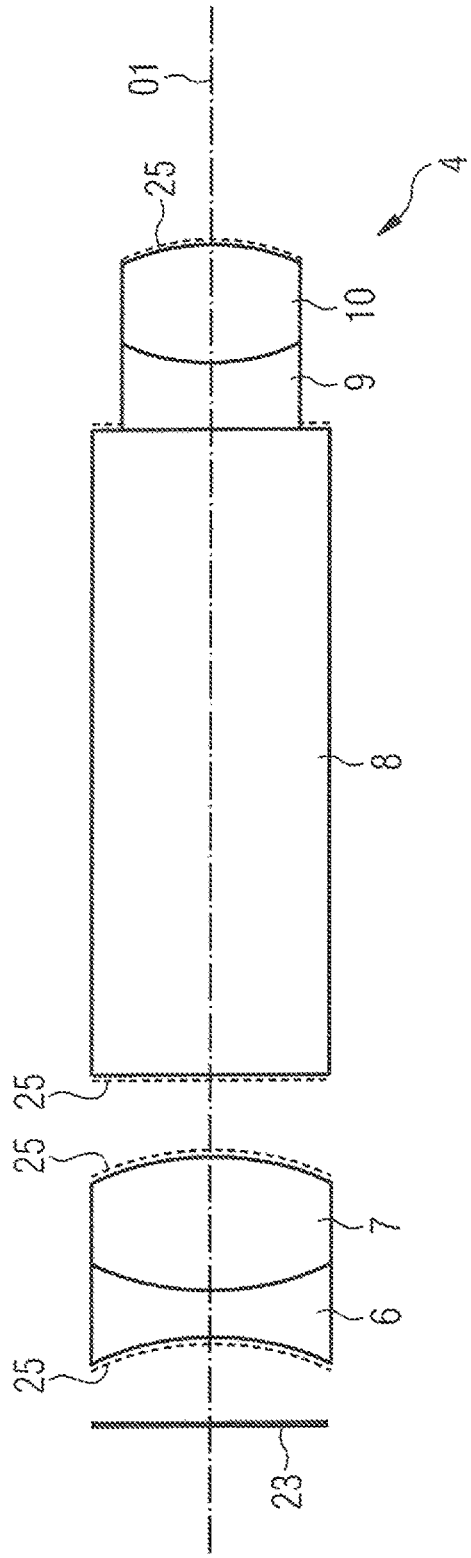
FIG. 2 shows an exemplary eyepiece optical system of the camera objective lens according to FIG. 1.

The eyepiece optical system 4 comprises several lenses 6 to 10, in particular a rod lens 8, and is described in more detail in FIG. 2. Advantageously, the eyepiece optical system 4 is designed to correct image errors of an upstream optical system, for example of the optical relay system not shown in FIG. 1. These image errors can, for example, be an image field curvature.

Further, the camera objective lens 1 includes an adaptor optical system 5 arranged parallel or eccentrically to the optical axis O1 of the endoscope shaft of the endoscope. The adapter optical system 5 comprises several lenses 11 to 14. For matching image sharpness and magnification, a device 16 that allows the adjustment of the individual lenses 11 to 14 is arranged at the adapter optical system 5. FIG. 3 inter alia describes the adapter optical system 5 in more detail.

The necessary beam deflections are, on the one hand, caused by the object-side prism 2 which deflects the real intermediate image 23 that is corrected by the eyepiece optical system onto the adapter optical system 5. On the other hand, the image-side prism 3 deflects the beams of the adapter optical system 5 onto the sensor surface 20 (i.e. an image sensor), wherein the image sensor 20 is arranged parallel to the optical axis. Together with the eccentric arrangement of the adapter optical system 5, thus a particularly compact structure of the camera objective lens 1 is achieved. Further, for protection of the image sensor 20, a plane-parallel glass pane 15 is arranged between the image-side prism 3 and the image sensor 20.

In FIG. 2, a possible embodiment of the eyepiece optical system 4 arranged on the optical axis O1 is schematically illustrated. As shown in FIG. 2, the eyepiece optical system 4 comprises a biconcave lens 6, a biconvex lens 7, a rod lens 8, a plane-concave lens 9 and a biconvex lens 10. Further, FIG. 2 shows the intermediate image 23. In the embodiment shown, the lenses 6 to 10 are arranged in two lens groups. A first lens group is formed by the biconcave lens 6 and the biconvex lens 7. The two lenses 6, 7 of the first lens group are cemented to each other and form an achromat. Further, the eyepiece optical system 4 comprises a second lens group, consisting of the rod lens 8, the plane-concave lens 9 and the biconvex lens 10. The lenses 8, 9 and 10 of the second lens group are cemented to each other. The plane-concave lens 9 and the biconvex lens 10 are configured such that they form an achromat. The rod lens 8 is designed such that it minimizes the image field curvature of a preceding optical system, for example the non-illustrated optical relay system. Further, the rod lens 8 allows an adaptation of the length of the endoscope without increasing the shaft diameter. An air gap may be provided between the first and the second lens group.

To reduce scattered light, surfaces that are perpendicular to the optical axis O1 and are not in contact with other surfaces have an antireflection coating 25 (see FIG. 2).

FIG. 3 shows an image-side detail of a schematic illustration of the camera objective lens 1. This detail comprises the eccentrically arranged adapter optical system 5, the image sensor 20 and the prisms 2, 3 for beam deflection.

The object-side prism 2 causes a beam deflection from the optical axis O1 onto the optical axis O2 of the adapter optical system 5. The image-side prism 3 causes a beam deflection from the optical axis O2 of the adapter optical system 5 onto the image sensor 20 arranged parallel to the optical axis O1. In order to avoid a loss of light by transmission, the two prisms 2, 3 have a high-reflection coating 24 on those sides where the beam deflection occurs. For avoiding scattered light, further sides either have an antireflection coating 25 or a matt black coating 26 not shown in FIG. 3 (see FIG. 4).

The adapter optical system 5 arranged parallel to the optical axis O1 comprises a convex-plane lens 11, a meniscus lens 12, a biconvex lens 13 and a biconcave lens 14. The biconvex lens 13 and the biconcave lens 14 are cemented to each other and chromatically corrected. Further, the device 16 for adjusting the adapter optical system 5 is shown. The device 16 is particularly advantageous in a stereoscopic endoscope since by way of it the image sharpness and magnification can be set separately for each of the two image channels.

FIG. 4 shows an image-side detail of a schematic illustration of the camera objective lens 1. In contrast to FIG. 3, the view plane in FIG. 4 is parallel to the image sensor 20. This detail comprises the eccentrically arranged adapter optical system 5 and the prisms 2, 3 for beam deflection. What is particularly illustrated is the matt black coating 26 of the two prisms 2, 3, which serves to reduce scattered light.

Table 1 shows the lens data of the camera objective lens 1 according to FIGS. 1 to 4. The optically effective surfaces are numbered in Table 1 from the object side with 1 to 22. All length information is expressed in the unit [mm]. The names of the glasses is in accordance with the nomenclature of Schott.

TABLE 1

| Surface | Radius | Thickness | Glass | Diameter |
|---|---|---|---|---|
| Objekt | Indefinite | 0 | | 2.5 |
| 1 | Indefinite | 2.59 | | 2.5 |
| 2 | −9.12 | 0.5 | N-SF4 | 3.4 |
| 3 | 4.678 | 1 | N-LAF21 | 3.4 |
| 4 | −6.1 | 1.234 | | 3.4 |
| 5 | Indefinite | 14 | N-LAF21 | 3.4 |
| 6 | Indefinite | 0 | | 3.4 |
| 7 | Indefinite | 0.6999951 | N-SF15 | 3.2 |
| 8 | 8.64 | 1.45 | N-LAF21 | 3.2 |
| 9 | −14 | 4.1 | | 3.2 |
| 10 | Indefinite | 3 | | 3.6 |
| 11 | Indefinite | 19 | N-BK7 | 2.58688 |
| 12 | Indefinite | 3 | | 5.451527 |
| 13 | 22.16 | 1 | N-BK7 | 7 |
| 14 | Indefinite | 0.4999999 | | 7 |
| 15 | 15.125 | 1 | N-SK5 | 7 |
| 16 | 50 | 1.533036 | | 7 |
| 17 | 10.58 | 1.4 | N-LAK21 | 7 |
| 18 | −21.76 | 1 | LF5 | 7 |
| 19 | 6.2 | 11.9043 | | 5.8 |
| 20 | Indefinite | 7 | BK7 | 5.747444 |
| 21 | Indefinite | 0.5 | | 5.942784 |
| 22 | Indefinite | 0.5 | BK7 | 5.963899 |
| Aperture stop | Indefinite | 0.99 | | 5.977852 |
| Image | Indefinite | — | | 6.058665 |

Figure 5:
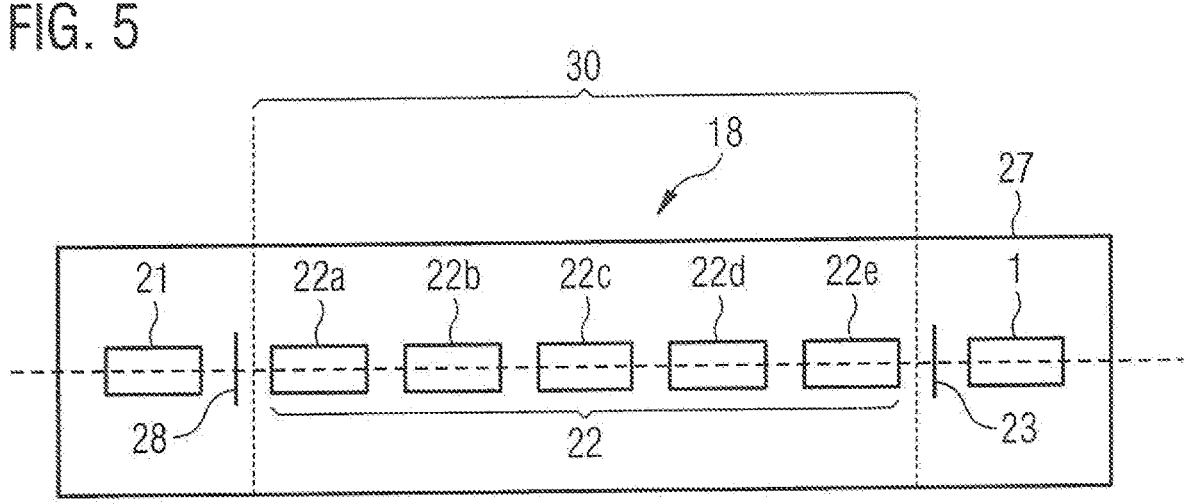
FIG. 5 shows a monocular endoscope according to one embodiment.

In FIG. 5, an embodiment of a monocular endoscope 18 is shown, which includes the camera objective lens 1 according to FIGS. 1 to 4. The monocular endoscope 18 comprises, as viewed from the object side, an objective lens 21, an optical relay system 30 with a relay module 22 with several relay module components 22a to 22e and the camera objective lens 1. Further, the endoscope 18 has a shaft 27 in which the afore-mentioned elements are arranged.

The objective lens 21 arranged at the distal end of the endoscope 18 generates an intermediate image 28 of the object to be observed. The relay system 22 images the distal first intermediate image 28 onto a proximal second intermediate image 23. In doing so, the relay system 22 transmits the first intermediate image 28 so to speak from the distal end to the proximal end of the endoscope 18. The camera objective lens 1 arranged at the proximal end of the endoscope 18 finally images the second intermediate image 23 onto the sensor surface 20 not shown in FIG. 5.

Figure 6:
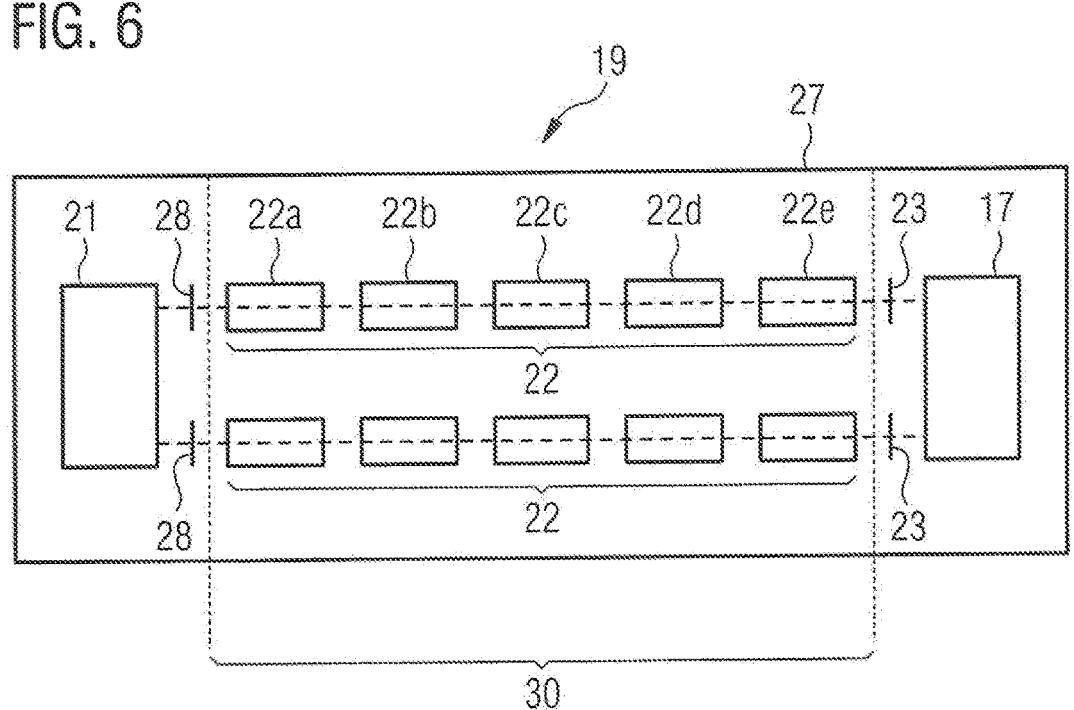
FIG. 6 shows a stereoscopic endoscope according to one embodiment.

An embodiment of a stereoscopic endoscope 19 is schematically illustrated in FIG. 6. In contrast to the monocular endoscope 18 illustrated in FIG. 5, the stereoscopic endoscope 19 has two optical channels. The stereoscopic endoscope 19 has a shaft 27 in which, as viewed from the distal end, an objective lens 21, a relay system 30 with two relay modules 22 (stereoscopic relay system) and a proximally arranged camera objective lens 17 are arranged.

The objective lens 21 images the object to be observed onto two distal intermediate images 28, each of which being assigned to one optical channel. The stereoscopic relay system 22 according to FIG. 6 images one of the two distal intermediate images 28 each onto one of the two proximal intermediate images 23 each. The camera objective lens 17 according to FIG. 6 is formed by two camera objective lenses 1 according to FIGS. 1 to 4. One of the two camera objective lenses 1 each is assigned to one of the optical channels. Each of the two camera objective lenses 1 finally images the proximal second intermediate image 23 onto the corresponding sensor surface 20.

The invention claimed is:

1. A camera objective lens for an endoscope, comprising
a first optical axis which extends along a longitudinal axis of an endoscope shaft, and a second optical axis which is offset relative to the first optical axis,
an object-side first prism and an image-side second prism,
a first lens system arranged on the object side of the first prism and a second lens system arranged on the image side of the first prism, wherein the first lens system is arranged along the first optical axis, and wherein the second lens system is arranged along the second optical axis, and
a sensor surface arranged at an image-side end of the camera objective lens parallel to the first optical axis,
characterized in that the first prism and the second prism are configured to cause a first to third beam deflection as a three-fold beam deflection so that by means of the first prism the first and second beam deflection is caused as a two-fold beam deflection from the first optical axis to the second optical axis and by means of the second prism the third beam deflection is caused as a simple beam deflection from the second optical axis to the sensor surface arranged parallel to the first optical axis,
that the first lens system includes a biconcave first lens, a biconvex second lens, a third lens formed as a rod lens, a plane-concave fourth lens and a biconvex fifth lens in this order as viewed from the object side,
and that the second lens system includes a convex-plane sixth lens, a seventh lens formed as a meniscus lens, a biconvex eighth lens and a biconcave ninth lens in this order as viewed from the object side.

2. The camera objective lens according to claim 1, characterized in that the first optical axis and the second optical axis are parallel to each other.

3. The camera objective lens according to claim 1, characterized in that the biconcave first lens and the biconvex second lens are cemented to each other.

4. The camera objective lens according to claim 1, characterized in that the third lens, the plane-concave fourth lens and the biconvex fifth lens are cemented to each other.

5. The camera objective lens according to claim 1, characterized in that the biconvex eighth lens and the biconcave ninth lens are cemented to each other.

6. The camera objective lens according to claim 1, characterized in that a plane-parallel glass plate is arranged parallel to the sensor surface between the second prism and the sensor surface.

7. The camera objective lens according to claim 1, characterized in that the biconcave first lens, the biconvex second lens, the third lens formed as a rod lens, one of the plane-concave fourth lens or the biconvex fifth lens of the first lens system or the convex-plane sixth lens, the seventh lens formed as a meniscus lens, and one of the biconvex eighth lens or the biconcave ninth lens of the second lens system each have an antireflection coating at their outer surfaces that are exposed to air.

8. The camera objective lens according to claim 1, characterized in that the first and second beam deflection occurs at a first surface and a second surface of the first prism, respectively, and the third beam deflection occurs at a third surface of the second prism, and that at least one of the first or second surfaces of the first prism or the third surface of the second prism has a high-reflection coating.

9. The camera objective lens according to claim 1, characterized in that at least one of the first prism or the second prism that are perpendicular to a beam path of the camera objective lens has an antireflection coating.

10. The camera objective lens according to claim 1, characterized in that at least one surface of the first prism or of the second prism that is perpendicular to the sensor surface parallel to the first optical axis has a matt black coating.

11. The camera objective lens according to claim 1, characterized in that the biconcave first lens, the biconvex second lens, the third lens formed as a rod lens, and one of the plane-concave fourth lens or the biconvex fifth lens of the first lens system or the biconcave ninth lens of the second lens system are made of flint glass.

12. The camera objective lens according to claim 1, characterized in that at least one of the convex-plane sixth lens, the seventh lens formed as a meniscus lens or the biconvex eighth lens of the second lens system or the first prism or the second prism is made of crown glass.

13. The camera objective lens according to claim 1, characterized in that the camera objective lens has a device comprising the second lens system for adjusting image sharpness and magnification.

14. A stereoscopic camera objective lens comprising
two camera objective lenses, each having a first optical axis which extends along a longitudinal axis of an endoscope shaft, and a second optical axis which is offset relative to the first optical axis,
an object-side first prism and an image-side second prism,
a first lens system arranged on the object side of the first prism and a second lens system arranged on the image side of the first prism, wherein the first lens system is arranged along the first optical axis, and wherein the second lens system is arranged along the second optical axis, and
a sensor surface arranged at an image-side end of the camera objective lens parallel to the first optical axis,
characterized in that the first prism and the second prism are configured to cause a first to third beam deflection as a three-fold beam deflection so that by means of the first prism the first and second beam deflection is caused as a two-fold beam deflection from the first optical axis to the second optical axis and by means of the second prism the third beam deflection is caused as a simple beam deflection from the second optical axis to the sensor surface arranged parallel to the first optical axis,
that the first lens system includes a biconcave first lens, a biconvex second lens, a third lens formed as a rod lens, a plane-concave fourth lens and a biconvex fifth lens in this order as viewed from the object side,
and that the second lens system includes a convex-plane sixth lens, a seventh lens formed as a meniscus lens, a biconvex eighth lens and a biconcave ninth lens in this order as viewed from the object side.

15. An endoscope comprising
at least one camera objective lens having a first optical axis which extends along a longitudinal axis of an endoscope shaft, and a second optical axis which is offset relative to the first optical axis,
an object-side first prism and an image-side second prism,
a first lens system arranged on the object side of the first prism and a second lens system arranged on the image side of the first prism, wherein the first lens system is arranged along the first optical axis, and wherein the second lens system is arranged along the second optical axis, and a sensor surface arranged at an image-side end of the camera objective lens parallel to the first optical axis, characterized in that the first prism and the second prism are configured to cause a first to third beam deflection as a three-fold beam deflection so that by means of the first prism the first and second beam deflection is caused as a two-fold beam deflection from the first optical axis to the second optical axis and by means of the second prism the third beam deflection is caused as a simple beam deflection from the second optical axis to the sensor surface arranged parallel to the first optical axis, that the first lens system includes a biconcave first lens, a biconvex second lens, a third lens formed as a rod lens, a plane-concave fourth lens and a biconvex fifth lens in this order as viewed from the object side, and that the second lens system includes a convex-plane sixth lens, a seventh lens formed as a meniscus lens, a biconvex eighth lens and a biconcave ninth lens in this order as viewed from the object side.

* * * * *